(12) United States Patent
Frederick et al.

(10) Patent No.: US 7,360,844 B2
(45) Date of Patent: Apr. 22, 2008

(54) GEOSTEERING DETECTORS FOR BORING-TYPE CONTINUOUS MINERS

(75) Inventors: Larry D. Frederick, Huntsville, AL (US); Dwight Medley, Fayeteville, TN (US); Roy W. Tivas, Esterhazy (CA)

(73) Assignee: The Mosaic Company, Plymouth, MN (US)

( * ) Notice: Subject to any disclaimer, the term of this patent is extended or adjusted under 35 U.S.C. 154(b) by 0 days.

(21) Appl. No.: 10/901,113

(22) Filed: Jul. 29, 2004

(65) Prior Publication Data

US 2005/0023881 A1    Feb. 3, 2005

Related U.S. Application Data

(60) Provisional application No. 60/490,443, filed on Jul. 29, 2003.

(51) Int. Cl.
E21C 25/34    (2006.01)
E21C 35/06    (2006.01)
E21C 35/24    (2006.01)

(52) U.S. Cl. .................... 299/1.2; 299/1.8; 299/1.4
(58) Field of Classification Search ............. 299/1.05, 299/1.8, 1.4, 1.1, 1.2
See application file for complete search history.

(56) References Cited

U.S. PATENT DOCUMENTS

| | | | |
|---|---|---|---|
| 3,421,796 A | | 1/1969 | Barrett |
| 3,578,807 A | * | 5/1971 | Barrett .................... 299/1.8 |
| 3,591,235 A | * | 7/1971 | Addison .................. 299/1.2 |
| 4,166,406 A | * | 9/1979 | Maughmer ............... 89/1.815 |
| 4,316,635 A | * | 2/1982 | LeBegue et al. ........... 299/80.1 |
| 4,968,098 A | | 11/1990 | Hirsch et al. |
| 4,968,978 A | | 11/1990 | Stolarczyk |
| 5,072,172 A | | 12/1991 | Stolarczyk et al. |
| 5,769,503 A | * | 6/1998 | Stolarczyk et al. ........ 299/1.2 |
| 5,810,447 A | * | 9/1998 | Christopher et al. ....... 299/30 |
| 5,863,101 A | * | 1/1999 | Seear ..................... 299/68 |
| 6,068,394 A | * | 5/2000 | Dublin, Jr. ................ 702/43 |
| 2002/0030400 A1 | * | 3/2002 | Frederick et al. .......... 299/95 |

FOREIGN PATENT DOCUMENTS

GB    2 027 094 A    2/1990
WO    WO 02/075361 A2    9/2002

* cited by examiner

*Primary Examiner*—John Kreck
(74) *Attorney, Agent, or Firm*—Patterson, Thuente, Skaar & Christensen, P.A.

(57) ABSTRACT

The invention provides, in one embodiment, a detector for a miner comprising a gamma sensing element and a light sensing element coupled to the gamma sensing element. According to the embodiment, the detector is mounted on a rotary cutter of a boring-type continuous miner such that the gamma sensing element has a view of a geologic formation being mined. A mining control system is also provided, comprising a miner having at least two rotary cutters and a gamma detector on each of the at least two rotary cutters for receiving gamma emissions from a geologic formation. The mining control system also provides an accelerometer and a rate gyro, wherein the accelerometer and the rate gyro correlate the received gamma emissions with positions of the at least two rotary cutters, and a central module that utilizes the correlated readings to determine whether the cutters should be moved.

11 Claims, 6 Drawing Sheets

SECTION A-A

GEOSTEERING DETECTORS FOR BORING-TYPE CONTINUOUS MINERS

This application claims the benefit of U.S. Provisional Application No. 60/490,443, filed on Jul. 29, 2003, the entirety of which is incorporated by reference herein.

BACKGROUND

For many years, attempts have been made to control rotary-type (boring-type) continuous miners through the use of gamma detectors and various other sensors. For those formations which contain characteristic radiation profiles, such as potash formations, gamma detectors have shown promise for controlling or assisting operators to control cutting. However, the results have generally been less than desired due to deficiencies in the gamma detectors, lack of system capabilities, and the manner in which the equipment has been employed.

There is a large economic value from being able to extract higher grade minerals while leaving the lower grade minerals in the mine. Not only is there a cost associated with cutting and removal of unwanted materials, but the good materials must be separated from waste materials and the waste materials must be disposed. There is also a need to calculate the grade of the ore being mined. Previous attempts at measuring the ore grade with gamma detectors have not been effective for some of the same reasons that the control of the cutting has not been effective. To measure the grade requires being able to actively measure the thickness of the beds, the radiation level from each bed, and to calculate the amount of material being mined from each bed. Previous and currently employed approaches do not provide sufficient precision for making accurate calculations, for reasons to be explained later.

Study of conventional attempts to control boring-type continuous miner cutting processes by use of gamma detectors has shown that when gamma detectors have been employed they have not been positioned properly in order to be able to make the needed measurements. Often, the detectors are located on the frame of the miner, 6-12 feet from the face of the formation being cut. Detectors located many feet from the face are measuring where the cutter has already passed instead of where the cutter is going. If a decision is made to move the cutter heads up or down, by the time that the gamma detectors can measure the effect of the decision, the mining machine, or crawler, will have climbed upon or dropped onto the newly cut floor that results from the cutting decision. In so doing, the effects of the cutting decision will be amplified and conditions are then set for an even more exaggerated response. Further, certain operational dynamics, if not corrected, will result in minor deviations from the ideal path, even if the formation is relatively constant. In addition, the detectors, being on the miner body, are located in fixed positions. Numerous fixed-position detectors, having specially selected fields of view, would be necessary to acquire precise radiation data from the beds to be observed. Physical limitations prevent using the needed number of detectors and make it essentially impossible to achieve the ideal fields of view.

There are thought to be many practical reasons why gamma detectors have not been placed near or on the rotating cutters of continuous miners. First is the difficulty of mounting a detector on the rotors, given the obvious space limitations and geometry. Either two or four rotors are used and these are interleaved as they rotate. If detectors are made small enough to fit in the available space, without interference with the opposing rotor, they may not be sufficiently sensitive. Another obstacle has been that most industrial gamma detectors cannot withstand the shock, vibration and abrasion associated with being near or on the cutter. Even if not broken by the environment, they are prone to produce false counts when subjected to shock or high vibration. These false counts degrade performance. Neither is it a simple matter to properly shield gamma detectors, while at the same time, maintaining a sufficiently large field of view, have good spatial resolution where needed, and be small enough to be properly positioned on a rotor.

Motion sensors or other suitable sensors, such as position sensors, and associated micro-controllers or processors are needed to correlate measurements with the position in the formation being mined and to process measurements from multiple beds of ore. Providing sufficient power to the sensors and transmitters on the rotor is another special need that must be addressed when locating the equipment on the rotor. Providing power to detectors on the rotors requires either battery modules or gravity-driven generators on the rotors, brushes (slip rings) to transfer power across the rotating shaft that supports the rotors or some other suitable mechanism. Transmitting data from the detectors to the control systems on the miner body is another challenge. Collectively, having to make these and other special provisions, in addition to the fundamental limitations of available detectors, have discouraged using a rotor-mounted gamma detector system or have resulted in disappointing failures.

The need for an effective boring-type continuous mining system remains. Rotor-mounted gamma detectors and associated hardware can produce a more effective control system but present many new problems to be solved.

U.S. Pat. No. 6,435,619, for example, the entire contents of which is hereby incorporated herein by reference, includes certain innovations generally directed to room and pillar mining or long wall mining using a drum-type continuous mining machine.

Although aspects of the present invention are amenable for use in the mining of numerous types of ores, the present invention will be described primarily in reference to the mining of potash, but it can apply to other types of mining where radiation exists in the formation. Underground mining of coal and trona are examples.

Vertical control of a continuous miner in a potash formation requires knowledge about the relationship of the miner to the mineral bearing beds in the formation as well as knowledge about the quality of the ore in those beds. Radiation from potash is generally proportional to the concentration of potash in the mineral bed. When there is a greater concentration of potash, the radiation level is also greater. By measuring the amount of radiation emanating from the mineral beds through which the miner is cutting, the position of the miner relative to these beds can be determined. Data from such measurements can also be used to determine the ore grade being mined.

Since the thickness of mineral beds vary, determining the position of the miner relative to a single bed is not a sufficient basis for good control. Accurate information about the thickness of the beds is also required. Or, said another way, it is necessary to know the position of multiple bed boundaries through which the miner is cutting. It is also important to know the quality of the ore in the beds at the top (also referred to as the "roof" or "back") and the bottom (also called the "floor") of the tunnel. Knowledge of position and ore grade allows systematic steering of the miner through the geologic formation so as to optimize the quality of the mineral that is mined.

Roll control is also needed to keep the miner aligned with the floor, which is often tilted from side to side. To accomplish roll control, i.e., tilt from side to side, knowledge of the relationship of the miner to the mineral beds on both sides of the miner is required. If gamma measurements are used as the basis for roll control, it is necessary to acquire gamma data from the walls on each side of the miner so that the cutter heads can be positioned to correspond with the tilt of the bed. Having done so, the miner will advance upon the newly cut floor, having a different tilt, side to side, and thus become realigned to the bed. As the tilt of the miner changes to match that of the beds being mined, the rotary cutter heads will return to their nominal orientation relative to the miner body. To achieve good control, the cutter heads must be made to respond to information about the formation at the cutter, ahead of the miner.

Since the mining equipment, including any gamma detectors being used, is radiated by all of the exposed surfaces of the formation being mined, sensors must be shielded from directions other than the target area for the bed of interest. In other words, the sensor must look for radiation coming only from the direction of the desired target area and not see the radiation from all other directions.

Minerals, such as potash, exist in layers or beds. Measurements made edgewise into the plane of a bed will produce data that is more easily interpreted than measurements made perpendicular to a bed. When looking perpendicular to the beds, it is difficult to determine which portion of the radiation is originating from the bed nearest the detector and which is emanating from beds farther away. This can be overcome to some degree by using spectral gamma data, rather than only gross gamma counts.

An ideal arrangement, if it could be achieved, would be to install a small detector near the tips of one arm on each rotor so the detectors could measure the radiation arriving in-plane from the beds in the face being cut. With this configuration, the detectors would exclusively be looking forward of the cutter. If it were achievable, having detectors positioned in this way should allow good vertical control. However, there are practical problems with implementing such an ideal arrangement. It would be very difficult, if not impractical, to attach sensors so that they could be extended and retracted along with the cutters on the rotors. Extendable cutters are necessary to avoid the cutters from getting wedged between the roof and the floor due to natural sagging of the roof as the tunnel is cut. Also, in order to provide a small field of view (FOV), encompassing a small solid angle regardless of the position of the rotor, a collimation device of considerable length is required, unless the scintillation element is made small. Adding a large collimation tube makes the job of mounting near the tips even more difficult. But, if the scintillation element is made small so that the shielded collimation tube is small, the count rate is too low to provide statistically accurate data. Further, if the FOV is made small compared to the scintillation element, the ratio of solid angle encompassing the target area in the formation is very small compared to the solid angle of all other directions. Then, a large amount of shielding becomes necessary to reduce background counts. Collectively, these considerations make it impractical to position a gamma detector near the tips, looking into the face.

Faced with the above problem, one might choose to place a detector further down on the rotor arm, nearer the hub. This is not satisfactory because the collimation requirement increases as well as shielding for the collimator, and neither space nor position allows typical detectors to be positioned such that they will be effective. The problem is perceived to be too difficult to overcome, particularly if conventional industrial gamma detectors are used. To overcome the above problems, a special combination of hardware design and system strategy is required.

There is a method and system architecture that will produce excellent results. A detector can be positioned on a rotor arm such that it is viewing in the radial direction into the surface of the circular path being cut out by the rotary cutter. If the detector has a low profile and does not extend very far down the rotor arm toward the hub, it will fit nicely and will be close to the mineral surface. This location is ideal for using a detector having a relatively large length to diameter ratio, due to a number of important reasons. First, it is important to provide a narrow field of view in the direction perpendicular to the beds but equally important to have a viewing area large enough to provide adequate sensitivity. A scintillation element size that is well suited for this application is 2 inches by 10 inches and should be oriented so that its long axis is parallel with the mineral beds. Having this shape, it is easier to configure the shielding to produce a FOV that is narrow in one direction, the direction in which good spatial resolution is needed, and wide in the other direction where spatial resolution is much less important. When the rotor arm is horizontal and the detector is looking horizontally into the beds, edge-wise, the narrow field of view is important to the rejection of radiation from beds above and below the one being measured. When the arm is vertical, good resolution is desired to detect the crossing of the interface at the roof. Having a wide FOV in the front-to-back direction, parallel to the mineral beds, increases sensitivity without reducing the resolution is the tangential direction for all rotor positions.

Another important advantage of using a scintillation element having an elongated shape is that it does not require much space above the rotor arm. This is particularly important for those rotor designs that have little space between opposing rotors. Also, the shape allows the entire detector to be placed near the end of the rotor arm so that it is beyond the path of the end of the arm on the opposing rotor, except for a section that can be low enough to not collide with the arm on the opposing rotor. If a conventional crystal configuration is used, having a round surface exposed to the radiation, a round collimation tube is required. This length of the tube must be at least twice the diameter of the crystal, and probably considerably longer in order to achieve acceptable spatial resolution. Instead, a detector, as proposed here, that has a relatively small diameter provides good spatial resolution and also makes room for adding more shielding to reduce background radiation thus improving the signal to noise ratio.

Some explanation may be helpful in better understanding the effect of detector FOV on sensitivity. The total sensitivity for a detector of a given size and type is the integration of the viewing area over the area of the crystal. It is more correct to say that the sensitivity is the integration of the volume of mineral emitting radiation to the detector over the volume of the detector. Since gamma rays have a wide range of energies, particularly after being scattered during their journey from their source to the detector, some will be stopped and counted near the surface of the scintillation element. The higher energy rays will tend to penetrate further into the scintillation element before being detected. Some will actually pass through the scintillation element and not be counted. Therefore, the total sensitivity of a detector is determined both by its exposed surface area and by its effective volume. For estimating and discussion purposes, it is sufficiently accurate to compare configurations based on areas rather than volumes so long as the average thicknesses of the scintillation elements being compared are reasonably similar.

This greater sensitivity is critical for a rotor-mounted detector because the view is constantly moving as the rotor turns. Data from each segment of the tunnel wall, roof and floor must be collected and summed over time in order to acquire enough data to overcome the statistical nature of radiation. Less sensitive detectors require more time to acquire the necessary data set.

In order to better understand the significance of the shape factor for a detector, a simplified discussion of the relationship of the detector shape and the desired FOV shape shows the importance of the factors. Consider a typical industrial gamma detector having a scintillation element that is 4 inches in diameter by 2 inches thick. On many miner rotor designs, there is not room for mounting a properly shielded detector that contains a 4 inch diameter crystal. But, assuming that there is room for a detector of that size, starting with the 4 inch diameter crystal and adding the materials necessary to support and protect it from the vibration environment and then adding thick shielding over the detector and over the collimation tube, results in additional height of at least 3 to 4 inches. Further, the collimation tube must be adequately long to sufficiently limit the FOV in the tangential direction, making the detector at least 8 inches high, and probably more. It is reasonable to assume that the collimation tube length will be at least twice the diameter of the scintillation element. This forces the center of the scintillation element to be approximately 20 inches away from the surface of the mineral. At 20 inches the main FOV, the area on the surface of the mineral that is in view of all the front surface of the scintillation element is approximately 20 square inches, or a circle that is approximately 5 inches in diameter. More importantly, the partial FOV that sees at least 50% of the volume of the scintillation element is approximately 75 square inches and is a circle approximately 10 inches in diameter. The cross-section surface area of such a 4 inch diameter crystal would be approximately 12.6 square inches. The sensitivity of the partial FOV will relate approximately to the product of 75 square inch partial FOV and the 12.6 square inch area.

In comparison, a properly designed 2 inch by 10 inch detector has a surface area of 20 square inches. The volume of the long crystal is also 25% greater than a 4 inch diameter by 2 inch thick crystal. Yet, it can be placed within about 10-11 inches from the mineral surface. Its height will be only about 65% that of the industrial 4 inch detector. The partial 50% FOV of this long detector in the tangential direction can be easily constrained to be only 9 inches, or less if desired, while its 50% partial FOV in the longitudinal direction, parallel to the plane of the bed, may be as much as 40 inches. A 9 inch by 40 inch FOV provides 360 square inches of viewing area which can be integrated over a crystal surface of 20 square inches. The partial FOV for this crystal will also be roughly related to the product of 360 and 20. After allowing for the distance factors, it is clear that the elongated crystal is much more sensitive. Given this greatly improved sensitivity, as compared with the 4 inch diameter scintillation element, the FOV of the 2 inch by 10 inch scintillation element can be reduced further as needed in the longitudinal direction and still maintain adequate sensitivity. But, in contrast, to reduce the field of the partial view of the 4 inch detector, the length of the collimation tube must be increased, when its-length would already a major problem for at least some rotor designs. In so doing, its already low sensitivity would be further reduced.

A gamma detector must have a light sensing device, such as a photomultiplier tube (PMT), to convert light flashes, produced by the scintillation element, into electrical signals. This PMT further increases the length of the gamma detector when length is already a serious problem. One option that might be considered would be to place the PMT inside the collimation tube, between the scintillation element and the source of the radiation. Although this is feasible, it is obviously undesirable because it blocks incoming radiation, particularly the lower energy radiation. These considerations again force one to consider using a smaller crystal, producing an overall smaller detector, and causing a serious loss of detector sensitivity. Again, there is an advantage to using the crystal shape proposed here because the smaller diameter makes it possible to use a smaller PMT, having a smaller face for light to enter. This is further improved upon by placing the PMT inside the hermetically sealed housing, with the scintillation crystal, so that window between and one optical coupler can be eliminated. Other special detector design features allow further reducing the length of the detector.

As can be understood from the foregoing discussions, there is a strong competition between the space available, the field of view needed, collimation requirements, a sufficiently large scintillation element, and shielding requirements. A typical industrial detector, having a circular scintillation face surrounded by a collimation tube, is not well suited to satisfy the configuration, performance, and reliability requirements. The above discussions were based on a hypothetical 4 inch diameter scintillation element in order to make a more understandable comparison. In reality, most, if not all, of the industrial detectors currently being used on boring-type continuous miners, are in fixed positions on the miner body, and have scintillation elements that are only 2 or 3 inches in diameter. Although these sizes are easier to integrate onto a rotor, their sensitivity is a serious limitation.

Since a detector on a rotor is moving rapidly, typically about 90° per second, the amount of gamma radiation that can be measured on a single revolution is not sufficient for control of the miner. Even for a highly sensitive detector configuration and location as already described, it remains necessary to accumulate gamma data over time for each segment of interest. A miner of this type is typically advancing slowly, between 1 and 2 feet per minute, and changes in the tilt of the formation occur slowly, over many feet of travel, the readings from many revolutions of the rotor can be combined. Also, undesirable excursions by the miner due to operational dynamics are usually small in a 1 to 2 minute period. Therefore, it is feasible to combine gamma data for multiple revolutions. To combine the data from many revolutions requires a method to correlate each gamma count with a position and to sum the measurements made for each position. This will be described in more detail later.

Some scintillation materials, such as sodium iodide, are very fragile and easily damaged. Gamma scintillation elements are also known to produce false counts under vibration and shock, requiring special packaging to be made noise-free. In order to fabricate a scintillation element, particularly one having a relatively large length to diameter ratio, such as a 2 inch diameter by a 10 inch length, special packaging is required for multiple reasons. This will be described in detail later. In order to conserve space, the size of the detector must be made as small as possible while still providing a suitably sized scintillation element. Provisions have been made in this invention to make the detector as compact as possible as will be described in detail later.

A well-designed gamma detector for this application provides for the photomultiplier tubes (PMTs), or other light detecting devices, to be directly coupled to the scintillation crystal with an oil-ringed coupler or some other reliable, high efficiency coupling. Elimination of the window that is normally between the PMT and crystal helps to achieve the highest possible performance. The design must be a very rugged, compact design which is crucial to achieving the needed performance within the limited space available. It must withstand the forces from mining, shock, vibration, and abrasion. Support of the critical PMT/scintillation element within the detector can be accomplished by metallic supports (such as flexible sleeves). Similar flexible sleeves, of a special dual-type, support the electronics and motion sensors in the armor. These devices provide excellent dynamic properties and use a minimum of space. The flexible sleeve for the scintillation element has gaps to minimize attenuation of incoming gamma radiation. The light sensing element, such as a PMT, must be a rugged type. This armor should be lead-filled, or be fabricated using a strong, high density metal such as tungsten, in order to reduce background radiation. A non-metallic high strength window is used in the armor to protect the scintillation element and other hardware from the ore being mined while providing little attenuation of the incoming gamma rays.

Rate gyros are used to determine the direction that the detectors are pointing so that gamma counts can be correlated with position. An accelerometer is used to remove long term drift, or offset, from the gyro outputs and to relate the positions of the rotors relative to gravity. An alternate method for removing long term drift from the rate gyro measurement may include magnetic switches or mechanical switches, proximity switches, laser beams, shaft position indicators, acoustic sensors, etc. For example, a magnet can be placed on the opposing rotor such that it will trip a magnetic sensor in the detector assembly whenever the opposing rotor approaches the rotor on which the detector assembly is located. It is possible to place such a magnet at other locations on the miner. Use of the accelerometer is preferred technically because it is an independent measure relative to gravity, can be contained entirely within the detector assembly, and does not require any external support.

Each detector contains the electronics, within the control module, required to acquire and transmit data and/or decisions to the miner and to each other. Typically, these electronics include at least three micro-processors, one for gamma, motion and logic control. The logic control section acquires data from the other two, makes logical decisions, and then sends the decisions and data to the miner as needed. If one detector is a master and the other a slave, most of the decision making is in the master. PIC microcontrollers are preferred to perform these processing functions because of their small size and low power requirements.

Passing data from one detector, sometimes called a Slave Detector, to another detector, called a Master Detector, can be accomplished by different techniques. RF transmitters and receivers are available in very small packages and can be integrated into the detectors for this purpose. Also, the data can be sent from one detector through brushes, slip rings, or encoder assemblies to the miner frame and then be sent through a second set of brushes, slip rings, or encoder assemblies to the detector on the other rotor. Information can be transmitted in both directions, using such techniques, as needed. Signal drivers are included in the control module to ensure adequate signal-to-noise ratio for that data transmitted by any of these techniques. Also, data and/or cutting decisions from the detectors may be sent to the miner in a similar manner.

In addition to sending cutting decisions to the miner control hydraulics, data may be transmitted for display to the operator. The control module will divide the full rotation of the rotor into many segments around the circumference. A typical segment would be 4 inches along the circumference. Gamma radiation is recorded continuously and gamma counts are correlated with the segment in its field of view. If a detector is added to the second rotor for roll control purposes, the data from that detector will be automatically associated with the appropriate segment, which will be in a different position in the cycle of the second rotor. Once on each rotation, the radiation detector will send the data along with steering decisions, via an RF link, collected on the previous revolution of the rotor. If an RF link is used, in order to save power, the RF transmitter may only be turned on for a brief time on each revolution and at the time when the rotor is in the best position for transmission. If the miner is equipped with slip rings for each rotor shaft, that would be a preferred arrangement, eliminating the need for RF equipment.

A special power source may be required for the portions of the geosteering system on the rotor. This can be provided by a set of nickel cadmium batteries that are located in another armored box located near the detector. Examples of other means of providing power to the system are to utilize a gravity driven system, or provide a means of transferring power from the miner across the shaft to the rotor.

SUMMARY

In one aspect, the invention provides a detector for a miner, comprising a gamma sensing element and light sensing element coupled to said gamma sensing element. The invention further provides that the detector is mounted on a rotary cutter of a boring-type continuous miner such that the gamma sensing element has a view of a geologic formation being mined.

In another aspect, the invention provides a mining control system comprising a miner having at least two rotary cutters, a gamma detector on each of the at least two rotary cutters for receiving gamma emissions from a geologic formation, and an accelerometer and a rate gyro, wherein the accelerometer and the rate gyro correlate the received gamma emissions with positions of the at least two rotary cutters. The invention further provides a central module, wherein the central module utilizes the correlated readings to determine whether the cutters must be moved.

In yet another aspect, the invention provides a mining control system comprising a miner having at least two rotary cutters and a gamma detector on each of the at least two rotary cutters. The invention also provides a means to correlate gamma ray readings with positions of the cutters, and a means to combine the position-correlated gamma ray readings to determine whether the at least two rotary cutters should be moved either up or down in order to place said miner in a higher grade ore.

Therefore, the invention provides an apparatus and method for using the apparatus that address a need in the mining industry. These and other features and advantages of the invention will be more clearly understood from the following detailed description and drawings of preferred embodiments of the present invention.

DETAILED DESCRIPTION OF PREFERRED EMBODIMENTS

As described above, gamma detectors are good candidates for being used to geo-steer boring-type continuous mining machines to bore through mineral bearing or ore bearing formations. Two of the most important considerations in creating an accurate method of geo-steering a miner through a geologic formation, having mineral beds of variable thickness and differing qualities, is the location of the gamma detectors and their field of view. The object is to steer the miner cutters (FIG. 1) in response to measurements made of the formation through which the miner is boring or cutting. The approach that has traditionally been taken is to mount detectors on the miner frame at distances of 4 to 12 feet behind the face being cut and measure the gamma radiation from the top, bottom and sides of the tunnel. Since the mineral beds are varying in thickness and the location of the miner relative to these beds is changing, whether due to intentional steering decisions or due to changes in the formation itself, it would take many gamma detectors to accurately measure the location of the bed boundaries if they are in fixed positions. Also, the FOVs of those detectors would have to be very precise, a requirement which imposes some very serious constraints on the size of the detectors and on their sensitivity. Extremely complex algorithms would be required to separate the many variables that such an approach would create. In view of these serious obstacles, the traditional approach is to use a few conventionally designed detectors and only attempt to make general approximations about the bed boundaries and the position of the miner relative to them. A much better solution is to mount the gamma detectors, that are suitably designed for this environment, on the rotary cutters such that they are viewing radiation coming from the beds and to do so with FOVs that are optimized for this purpose. An exemplary explanation as to how this can be achieved follows.

Figure 1:
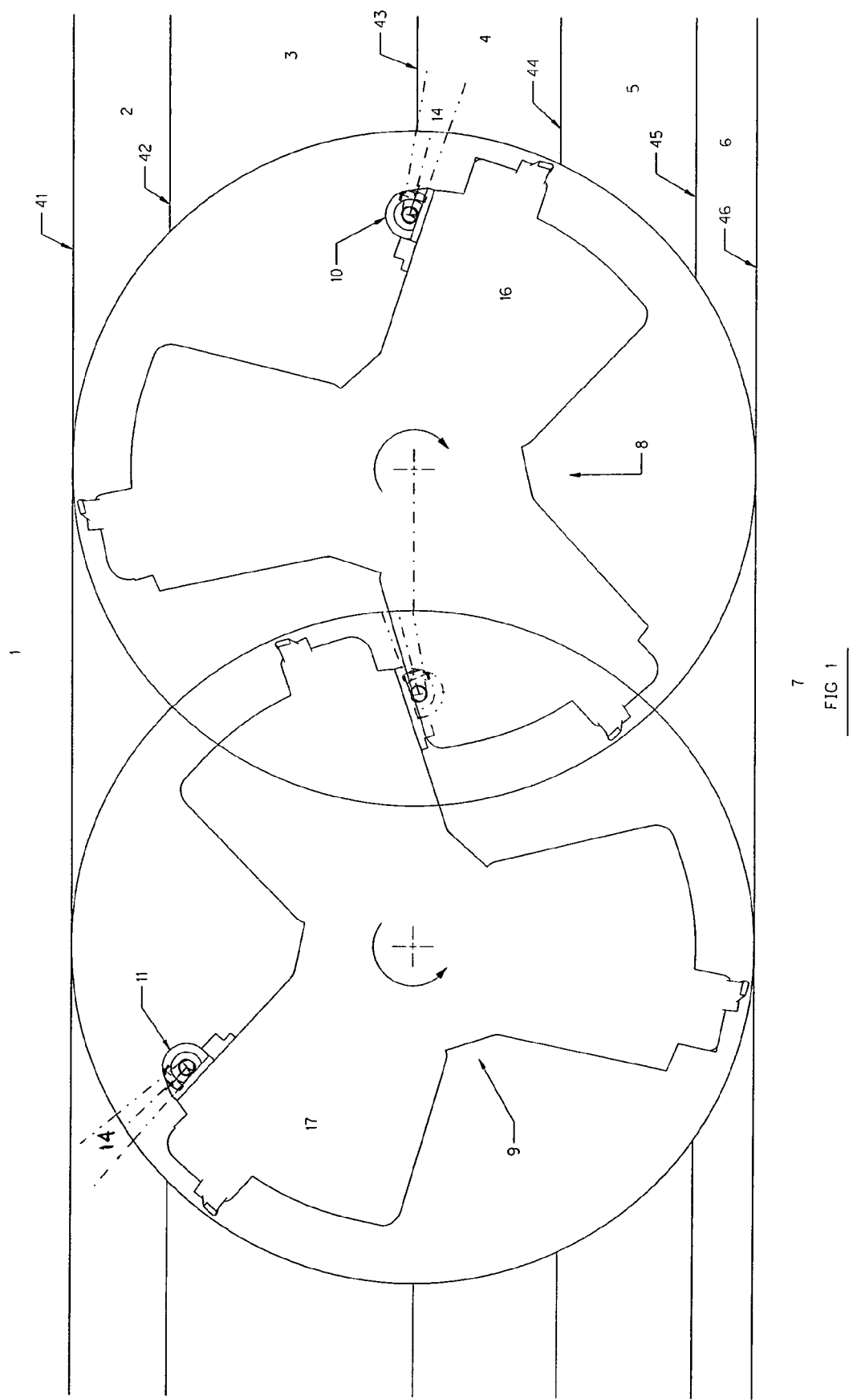
FIG. 1 is a view illustrating detectors on arms of a dual-rotor continuous miner in accordance with an embodiment of the invention.
Figure 6:
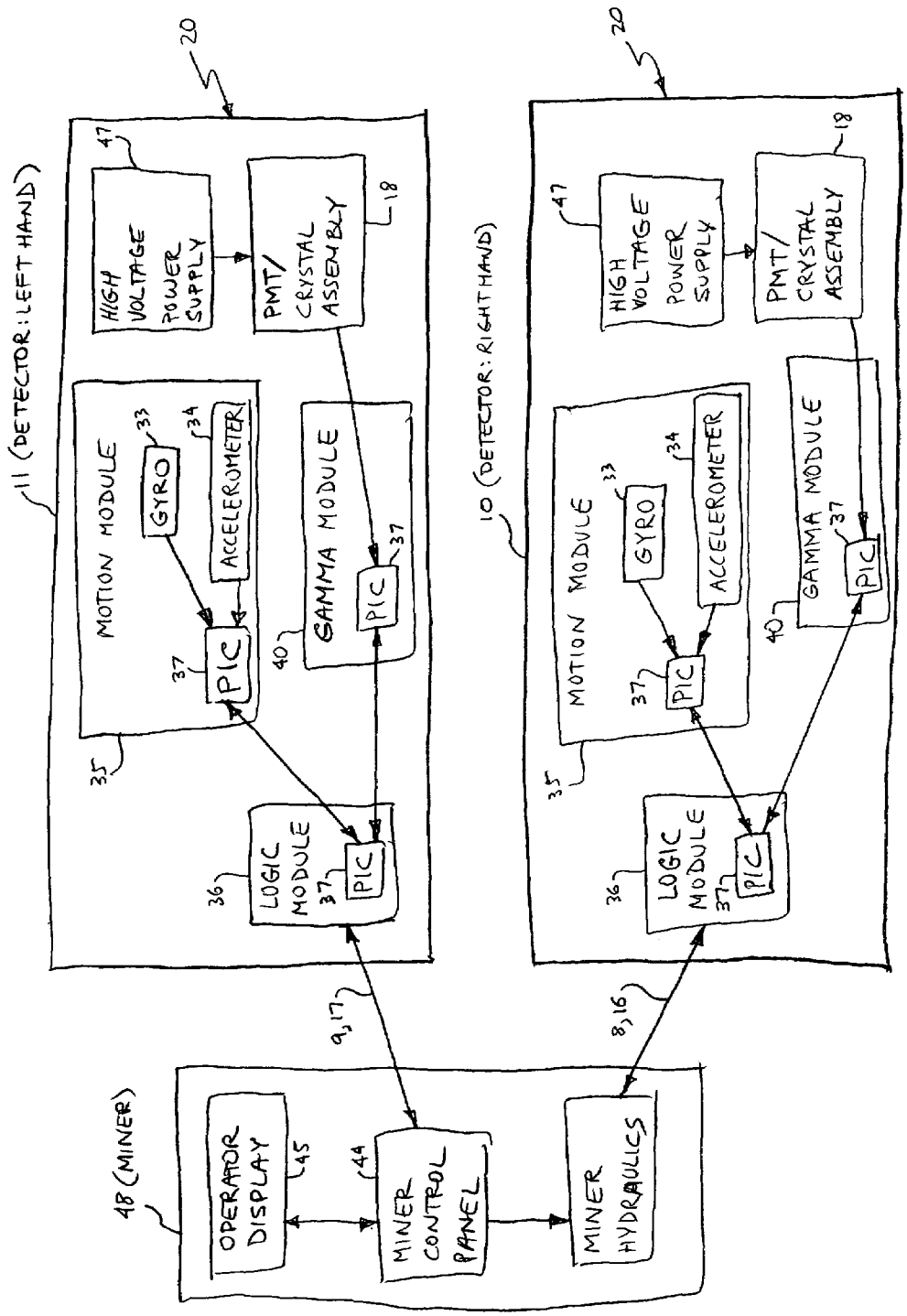
FIG. 6 is a diagram of data flow.

Boring-type continuous miners remove minerals from a mineral formation by boring a tunnel. As shown in FIGS. 1 and 6, two detectors 10, 11 are mounted on rotor arms 16, 17 on a miner 48 that is advancing in a direction perpendicular to the plane that includes the detectors 10, 11. One rotor 8 rotates in a clockwise direction and the other rotor 9 rotates counter-clockwise. While some boring-type continuous miners have four rotors, the following discussions apply to both. In the case of a four-rotor miner, the discussions will concern the two outer rotors.

The formation indicated in FIG. 1 is assumed to be composed of layers 1-7, or beds, each of which has a mineral composition of differing quality. These layers 1-7 vary somewhat in thickness and may be tilted in any direction and the tilt frequently may change somewhat. It is thus important to map the thickness, location and quality of various layers 1-7 as the miner cuts through the formation so that decisions may be made as to whether the miner should be cutting higher or lower in order to remove the highest quality ore.

Figure 2:
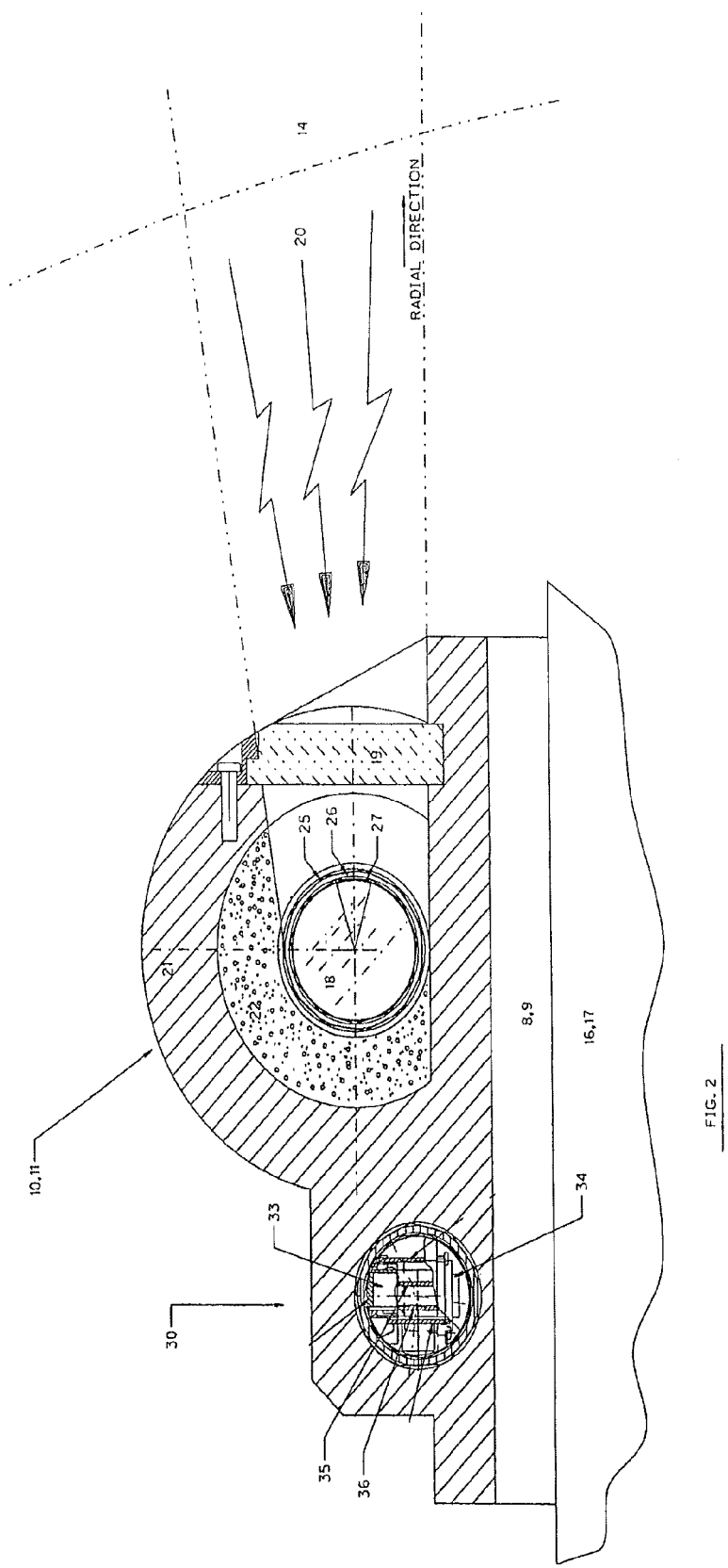
FIG. 2 is a cross sectional view of a detector of FIG. 1 indicating a field of view.
Figure 3:
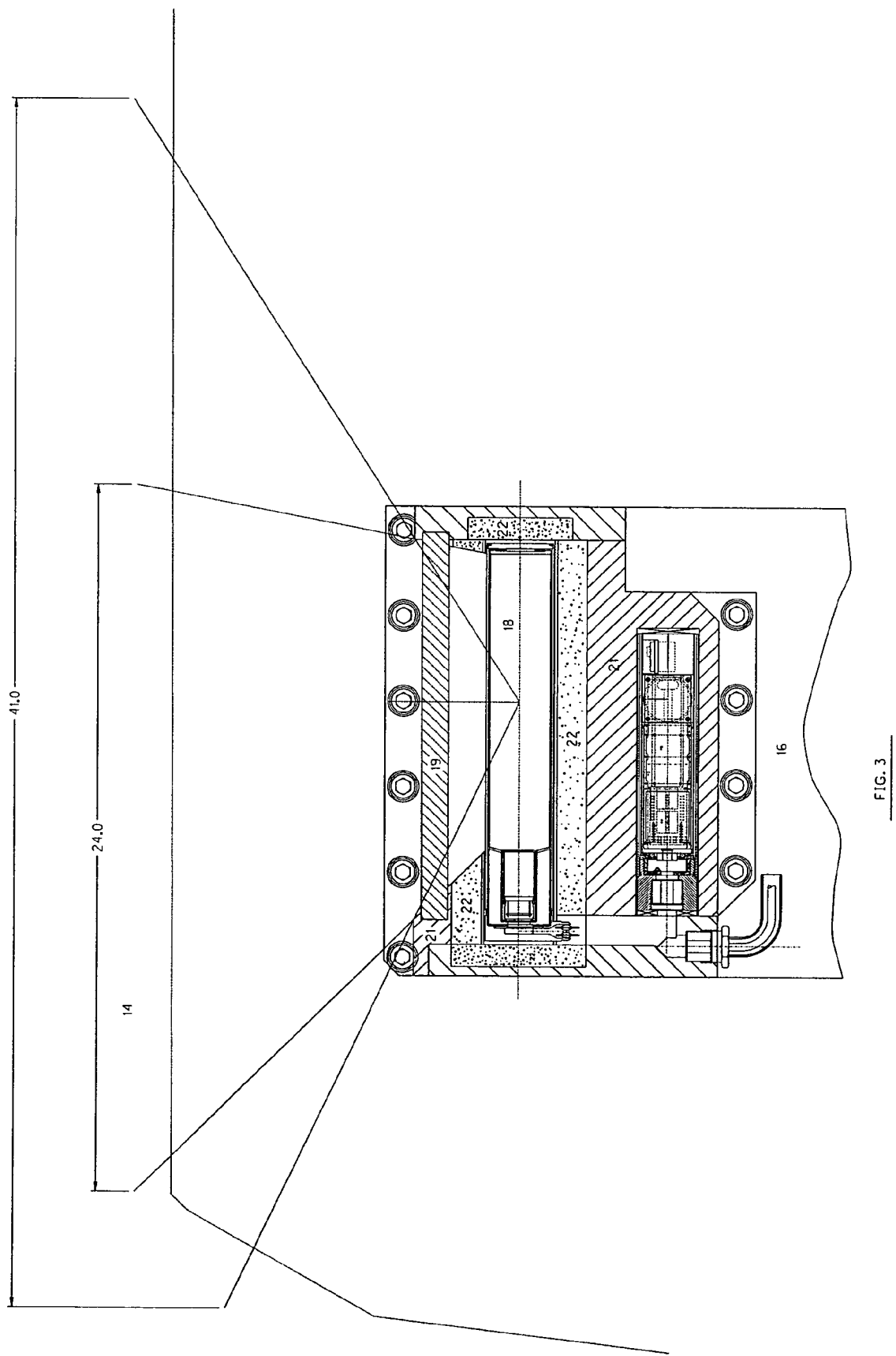
FIG. 3 is a cross sectional view of a detector of FIG. 1 indicating a field of view.
Figure 4:
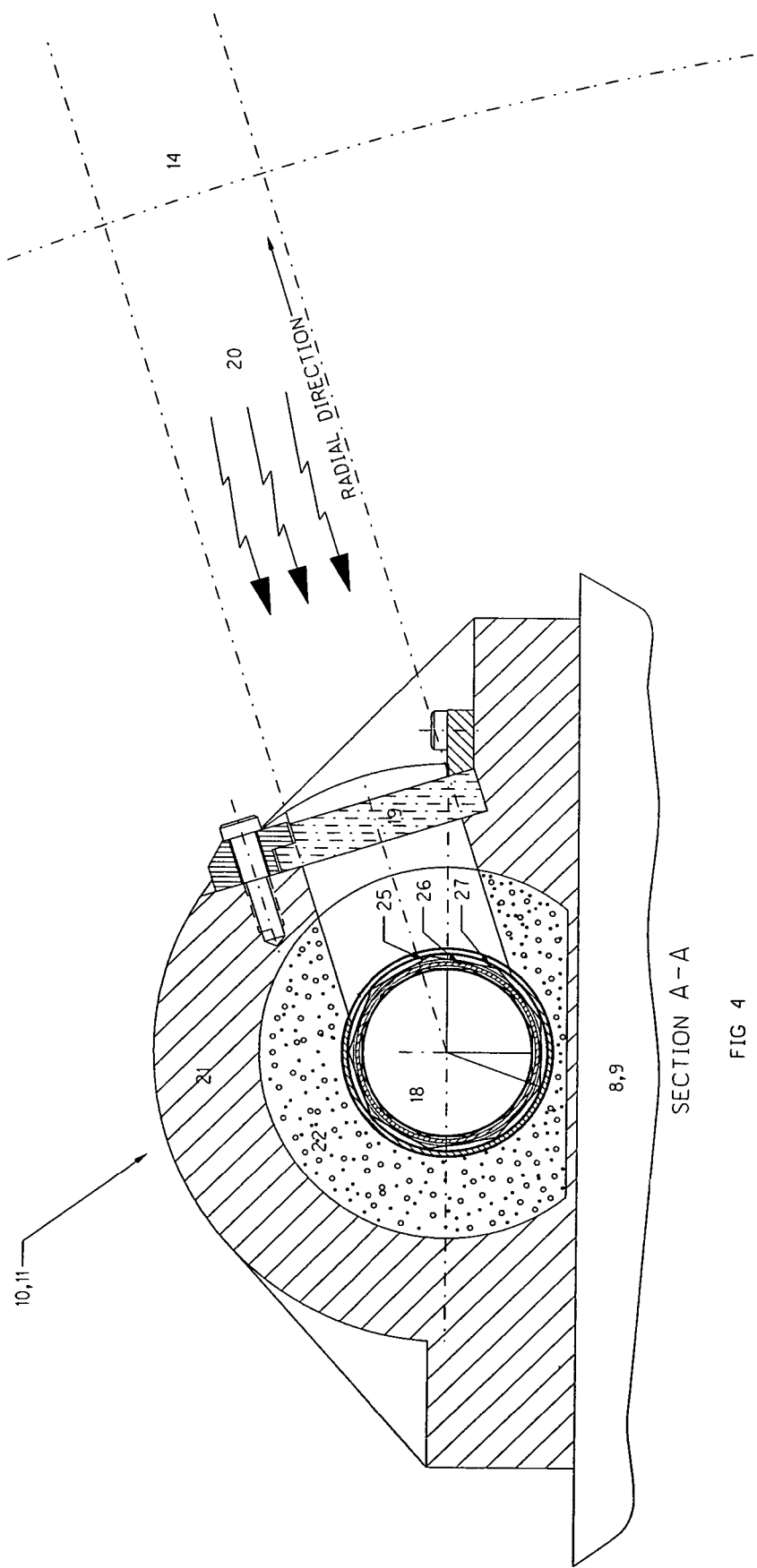
FIG. 4 is a cross sectional view of a detector in accordance with an embodiment of the invention.
Figure 5:
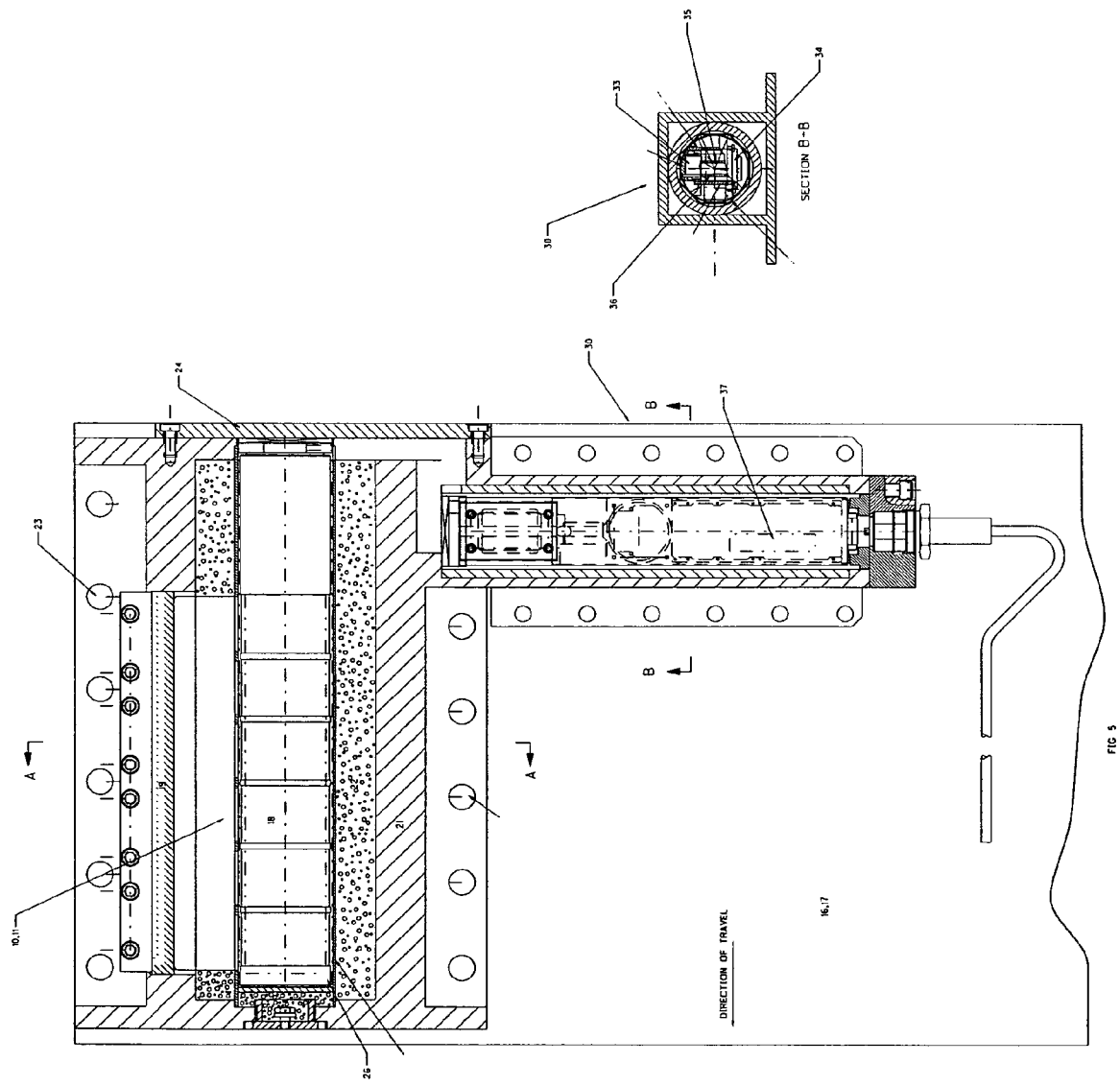
FIG. 5 is a top view of a detector in accordance with an embodiment of the invention.

By placing the detectors 10, 11 at the end of rigid sections of, respectively, rotor arms 16, 17, they are within about 11 inches of the mineral surface and very near the face that the cutters are advancing into. The gamma sensing element in the detector has been shaped and oriented to allow the field of view (FOV) to be small in the direction needed to identify bed boundaries 41-46 as illustrated in FIGS. 1, 2 and 4, while being large in the direction parallel with the beds as illustrated in FIG. 3. The combination of making the sensing element small in tangential direction and of placing the element close to the mineral surface allows measuring the surface in small segments as the rotors 8, 9 rotate. Equally important, the combination of making the sensing element ten inches long and making the FOV to have a long dimension in the plane of the bed boundaries 41-46 also provides for high sensitivity to each bed as it sweeps past it. This sensitivity is essential to having a high enough count rate to be able to achieve a high spatial resolution. By use of this arrangement, the competing requirements on the detector, small FOV and high sensitivity, are both satisfied.

To identify the bed boundaries 41-46, it is necessary to have count rates on each side of each boundary 41-46 that are distinctively different from those on the other side of the boundaries. As the detector FOV sweeps past the bed boundaries, the change in gamma rates must be measured with sufficient accuracy and resolution to allow making accurate cutting decisions. If conventionally configured industrial gamma detectors are employed, and if they are positioned perhaps 20 inches from the surface, particularly if the detection surface facing the formation is circular, spatial resolution is seriously degraded and/or much sensitivity is lost, and thus it would seem not feasible to use this approach. Given that radiation is statistical in nature, if the count rate is low, it is not possible to distinguish one side of the boundary from the other side. In fact, this challenging issue has been a major limitation to earlier approaches and has probably been one of the deterrents from others attempting to mount gamma detectors on the rotors.

Located on an arm 16, 17 of each rotor 8, 9 is an armored gamma detector 10, 11, configured to measure radiation being emitted from the formation 6 that is being mined. The reason for having two detectors and the way in which they cooperate will be discussed later, following discussion of certain details, most of which apply to either of the detectors 10, 11. Discussion is directed to one detector, but the discussion is applicable to both. An exception is when one detector is made into a Master Detector and the other a Slave Detector. In this case, the Slave Detector can have somewhat reduced capability.

The main field of the detector 10 shown in FIG. 2 is viewing a segment 14 of the surface exposed by the mining operation. Inside the detector 10 is the gamma sensing element 18, that typically is about 2 inches in diameter by 10 inches long. Notice that the main FOV, the FOV that subtends an area that is fully visible to the cross-section of the scintillation element 10, is only a small segment of the surface cut by the rotor 8, 9. As the rotors 8, 9 turn through a complete revolution, the surface being cut by each rotor 8, 9 can be thought of as having many segments 14, one adjacent to the other. A typical arrangement would be to divide the total circumference of the rotor 8, 9 into 75-100 segments, each 3-4 inches long. Referring to FIG. 3 it can be seen that the length of the "full" FOV, a view that exposes the full length of the crystal, is about 24 inches.

Gamma detectors 10, 11 are configured so they can be mounted at the end of the rigid portion of arms 16, 17. It will help to clarify that the tips 24 of all rotor arms, including arms 16, 17, on which the detectors 10, 11 are mounted, are retractable. When the miner pauses or stops cutting, these tips are retracted so that settling of the top of the newly cut tunnel will not trap or pinch the rotors 8, 9 between the sagged roof of the tunnel and the floor. When the rotors begin to turn, the tips extend out to make the rotors 8, 9 their full size for cutting. Therefore, the detectors 10, 11 must be mounted on the rigid portion of the arms 16, 17.

With reference to FIGS. 2-5, detector 10 includes a central portion having a scintillation element 18 that produces a flash of light or scintillation when gamma rays 20 from the formation strike it. The scintillation element is typically encased in a shield 26, which will be hermetically sealed if using a sodium iodide crystal or other hygroscopic crystal. The light flash created by the gamma rays 20 converted to an electrical pulse by a device, such as a photomultiplier tube (not shown in the figure). It is preferred that this PMT be located inside the housing with the scintillation crystal, directly coupled to the crystal for highest performance and smallest size. However, it may be external to the crystal housing, or shield, and receive the light flashes through a window. Dynamic supports of the detector elements include flexible sleeves 25, 27. Surrounding the scintillation element is a lead barrel 22 that has a window opening for gamma rays 20 to pass through to the scintillation element 18. Surrounding the lead 22 is armor 21. A one inch thickness of lead 22 and one inch steel armor 21 is recommended for adequate shielding and protection from mining materials. The window opening is covered with a strong, non-metallic material 19, such as polyether ether ketone (PEEK), to keep the mined minerals from striking the shield 26 around the scintillation element 18. This window cover 19 also keeps the materials from interfering with the operation of the flexible sleeves 25, 27 which protect against vibration and shock. A high voltage power supply 47, shown in FIG. 6, supplies power to the PMT/scintillation assembly 18.

With a detector of the type described above mounted on each rotor and positioned to look in the radial direction, excellent sensitivity and spatial resolution will be available. Even though these most basic needs are fully satisfied, alone these capabilities cannot produce usable data for control purposes. Since the rotors are constantly moving, the gamma readings being made are of no use unless it is known where the detectors are looking when each gamma ray is counted. Rugged, solid state gyros are available that can provide an accurate measurement of the movement of the rotor. By properly reading a rate gyro, the complete revolution of the rotors can be divided into angular segments which correspond to spatial segments along the surface of the tunnel being carved out by the rotors. Gamma counts acquired while a detector is pointed toward a segment can be recorded and are then associated with that segment.

A rate gyro 33, shown in FIG. 2, is the most suitable device for this purpose. However, the rate gyro 33 measures rate of rotation, not position. In order to acquire data on each segment 1-7 of the formation, it is necessary to know the angular position of the rotors 8, 9 to know when the detectors 10, 11 are pointed to each segment 1-7 and measuring the radiation 20 from that segment. A method must be provided to identify a reliable reference from which the rate gyro 33 output can be integrated over time to calculate the position of the rotors. The preferred method for obtaining a position reference is with the use of an accelerometer 34. It is worth noting that it is possible to determine the position of the rotors by use of the accelerometer alone, without the use of a rate gyro but it will not be as precise due to the effects of vibration and shock.

One section of the armored detector shown in FIG. 2 includes a control module 30. Included inside the motion module 30 is the rate gyro 33, accelerometer 34, and the PIC processors or microcontrollers 37, shown in FIG. 6. These PIC processors 37 read the changes in position measured by the rate gyro 33 and also read the gamma counts being produced by the scintillation element 18. As gamma counts are being read they are correlated to the segment 1-7 being viewed at that time. Rotor arm positions 16, 17 are referenced to gravity using the accelerometer 34. When the accelerometer 34 is pointed toward the roof of the tunnel, it reads maximum and when it is pointed horizontally, it reads zero. Properly processed, the outputs from the accelerometer 34 allow determination of rotor 8, 9 orientations. Due to vibrations, the accelerometer 34 readings must be filtered or averaged and then adjustments are made to account for the delay in the results caused by the filtering or averaging. Readings from the gyro are integrated over time and used to "feed forward" the rotors 8, 9. Roll control requires knowing the position of the miner relative to the mineral beds on each side of the miner which is derived from the motion measurements and calculation. Final cutting decisions are made by a single detector, using information from both detectors. Data that is collected and processed by the Slave Detector 11 is transmitted to the Master Detector 10 on a continuous, real time basis, and is then correlated to the formations by the Master Detector 10. This flow of data through RF links or slip rings is indicated in FIG. 6. In order for the interleaved arms of the rotors 8, 9 to not collide, they are locked in synchronization by provisions in the miner. If there is not excessive backlash in the rotors, it is then a matter of determining the relative relationship between the direction each detector is pointed and then shifting the data so that the segments on both sides correspond to the same elevation on both sides. This is accomplished in the Master Detector 10, along with processing the data as required. Once the system is able to precisely correlate the measurements on both sides of the miner, the orientation of the miner around its axis of travel, relative to the mineral beds, can be calculated and the cutter heads can be positioned to match. As the miner climbs upon the roll adjusted floor, the head will return back to its nominal position unless the tilt of the floor is continuing to change. The Slave Detector may be configured to include a rate gyro and accelerometer to independently determine orientation of the rotor on which it is installed.

The control module 30 performs all processing of the gamma data and motion data to arrive at cutting decisions. Electrical pulses from the gamma scintillation detector assembly 18 are received by the gamma module 40 as indicated in FIG. 6. These pulses are binned according to their energy levels and counted. The total counts within each bin, corresponding to energy levels, as well as the total number of counts per time period, are then transmitted to the logic module when requested by the logic module.

Concurrently, measurements made by the accelerometer and the rate gyro are sent to the motion module 35 as indicated in FIG. 6. After processing by the motion module, the current position of the FOV relative to the rotor miner is transmitted to the logic module 36. The logic module 36 then correlates the gamma data with position and applies algorithms to determine the position of the miner 48 relative to the formation beds 1-7. Given the position of the miner 48 relative to the beds 1-7, decisions are made to align the miner 48 with the beds and to position the miner 48 vertically to stay within the formation so as to mine the highest grade mineral. These cutting decisions are implemented by commanding the rotors 8, 9 to be raised or lowered by use of the miner control panel 44 by use of the hydraulics 46. In case of coal, the objective, in general, is to bore in the direction of the lowest gamma radiation levels, whereas in the case of potash, the objective is to bore in the direction of the highest gamma radiation. Data, including cutting decisions, are also provided to the operator via a display 45. The operator can adjust how the miner 48 responds to the data and decisions from the Master Detector 10 and/or from both detectors 10, 11.

Other algorithms are applied to determine the overall grade of the ore being mined, for downstream product decisions. Each of three electronic modules 34, 35, 36 include a PIC microcontroller 37 which performs the required processing.

Given that provisions are made for counting gamma rays and processing these readings to determine the relative radiation strength for each segment in the revolution, this information must be acted upon. The PIC microcontrollers 37 in control module 30 apply a system strategy to analyze, compare, and make cutting decisions upon that data. Cutting decisions are then sent to the miner by various possible means. If the miner rotor shafts have been outfitted with suitable slip rings, that is the simplest implementation of the required information exchange. High speed rf/data technology can be employed if the miner is not so equipped. Remote monitoring of the miner performance can be achieved once the data has been sent to the miner.

In summary, design of detectors to have suitable shape, size, FOV, being highly compact but well shielded, having adequate shock and vibration immunity, and positioning those detectors on the rotors of a continuous mining machine is the first step in collecting the adequate, accurate data. The next major step is to provide a means for correlating the gamma measurements with position in the formation. Processing of the data acquired from each segment of the tunnel surface then makes it possible to determine the location of the bed boundaries and the grade of the ore in the beds. Finally, algorithms can be applied to the spatially correlated data to optimize the path of the miner through the formation and the logical decisions made by these algorithms can be forwarded to the controls that operate the cutter head. The result is effective geosteering of the miner.

While the invention has been described in detail in connection with preferred embodiments known at the time, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention.

What is claimed as new and desired to be protected by Letters Patent of the United States is:

1. A mining control system comprising:
a miner having at least two rotary cutters, each said rotary cutter having arms extended from the rotary cutter;
a gamma detector on each of said at least two rotary cutters for receiving naturally emitted gamma emissions from a geologic formation, wherein each gamma detector is mounted on one of the arms of the rotary cutter such that the gamma detector has a small field of view relative to identifying bed boundaries in the geologic formation and a large field of view in a direction parallel to the geologic formation;
a position correlating system to correlate said received gamma emissions with positions of said at least two rotary cutters; and
a central module, wherein said central module utilizes said correlated readings to determine whether the cutters should be moved.

2. The mining control system of claim 1, wherein said central module compares readings corresponding to positions of said at least two rotary cutters and determines which way said at least two rotary cutters should be moved to keep said miner aligned up and down with mineral beds in said geologic formation.

3. The mining control system of claim 1, wherein said central module transmits signals to hydraulic cylinders for moving said at least two rotary cutters in a direction required to guide said miner within said geologic formation.

4. The mining control system of claim 1, further comprising a display which displays gamma counts versus cutter orientation to an operator or to a remote monitor.

5. The mining control system of claim 1, wherein the small field of view relative to identifying bed boundaries in the geologic formation defines a plurality of adjacent viewing segments which are cooperatively equivalent to a rotary cutter circumference and wherein comparison of naturally emitted gamma emissions form each adjacent viewing segment allows the central module to distinguish the bed boundaries.

6. The mining control system of claim 5, wherein the plurality of adjacent viewing segments can include from about 75 adjacent viewing segments to about 100 adjacent viewing segments.

7. The mining control system of claim 5, wherein said central module combines data from adjacent viewing segments to calculate a grade of an ore being extracted.

8. The mining control system of claim 1, wherein each gamma detector is mounted on the corresponding rotary cutter such that a gamma sensing element in each gamma detector is located within about 11 inches of a face of the geologic formation being cut by the rotary cutter.

9. The mining control system of claim 1, wherein the position correlating system includes an accelerometer and a rate gyro to correlate the gamma emissions with the positions of the at least two rotary cutters.

10. The mining control of claim 1, wherein the position correlating system includes a pulse encoder to correlate the gamma emissions with the positions of the at least two rotary cutters.

11. A mining control system comprising:
a miner having at least two rotary cutters, the cutters having extending arms;
a gamma detector on each of said at least two rotary cutters, the detector being mounted on one of the extending arms of the rotary cutter such that the detector is within about 11 inches of a cutting face of a geologic formation, the detector having a field of view along the cutting face small enough to define between about 75 to about 100 adjacent viewing segments within a cutter circumference defined by each rotary cutter;
a means to correlate gamma ray readings of the adjacent viewing segments with positions of the cutters,
a means to combine said position-correlated gamma ray readings to determine whether said at least two rotary cutters should be moved either up or down in order to plate said miner in a higher grade ore.

* * * * *